United States Patent [19]

Matsen, III

[11] Patent Number: 5,037,437
[45] Date of Patent: Aug. 6, 1991

[54] METHOD OF BONE PREPARATION FOR PROSTHETIC FIXATION

[75] Inventor: Frederick A. Matsen, III, Seattle, Wash.

[73] Assignee: University of Washington, Seattle, Wash.

[21] Appl. No.: 466,777
[22] Filed: Jan. 18, 1990
[51] Int. Cl.$^5$ .............................................. A61F 2/28
[52] U.S. Cl. ................................................... 623/16
[58] Field of Search ....................... 604/35, 49, 54, 93, 604/119, 902; 128/897, 898; 433/180, 183; 623/16, 18, 19, 20, 22, 23

[56] References Cited

U.S. PATENT DOCUMENTS

| | | |
|---|---|---|
| 559,417 | 5/1896 | Spencer . |
| 2,812,765 | 11/1957 | Tofflemire . |
| 3,081,770 | 3/1963 | Hunter . |
| 3,085,573 | 4/1963 | Meyer et al. . |
| 3,208,145 | 9/1965 | Turner . |
| 3,228,393 | 1/1966 | Michele .................... 623/23 |
| 3,416,532 | 12/1968 | Grossman . |
| 3,542,017 | 11/1970 | Adams . |
| 3,578,884 | 5/1971 | Jacobson . |
| 3,660,899 | 5/1972 | Linkow ................... 433/176 |
| 3,889,675 | 6/1975 | Stewart . |
| 3,930,505 | 1/1976 | Wallach . |
| 4,012,842 | 3/1977 | Vit . |
| 4,016,651 | 4/1977 | Kawahara ............... 433/174 |
| 4,229,221 | 11/1981 | Phillips et al. . |
| 4,283,799 | 8/1981 | Pratt, Jr. et al. ........... 623/23 |
| 4,294,251 | 10/1981 | Greenwald et al. . |
| 4,336,618 | 6/1982 | Raab ......................... 623/16 |
| 4,364,394 | 12/1982 | Wilkinson . |
| 4,373,217 | 2/1983 | Draenest .................. 623/16 |
| 4,380,435 | 4/1983 | Raeder et al. ........... 433/180 |
| 4,397,640 | 8/1983 | Haug et al. . |
| 4,519,385 | 5/1985 | Atkinson et al. . |
| 4,526,573 | 7/1985 | Lester et al. . |
| 4,583,531 | 4/1986 | Mattchin ................ 128/66 |
| 4,662,829 | 5/1987 | Nehring . |
| 4,735,603 | 4/1988 | Goodson et al. . |
| 4,735,625 | 4/1988 | Davidson ................. 623/16 |

OTHER PUBLICATIONS

Zimmer, Inc., "Surgical Technique Harris/Galante Porous Hip Prosthesis", by William H. Harris, M.D., 1984.
Zimmer, Inc., "The Iowa Total Hip Design and Surgical Technique", by Richard C. Johnston, M.D., 1983.
Minnesota Mining & Manufacturing Company, "Surgical Protocol, Neer II Total Shoulder System, Arthoplasty of the Shoulder: Neer Technique", by Charles S. Neer, II, M.D., 1986.
Howmedica, Inc., "The PCA Total Hip System", 1984.
Howmedica, Inc., "Howmedica Surgical Techniques: Variable Axis Total Knee Surgical Technique", by David G. Murry, M.D., 1978.
Howmedica, Inc., "Howmedica Surgical Techniques: The Exeter Total Hip System", by R. S. M. Ling & A. J. C. Lee, 1982.
Howmedica, Inc., "Howmedica Surgical Techniques: Howmedica Kinematic II Total Knee System", by Frederick C. Ewald, Peter S. Walker & William H. Thomas, 1983.
Davol, Inc., "Simpulse Pulsed Lavage".
Krause et al., "Strength of the Cement-Base Interface", 1982.
Noble & Swarts, "Penetration of Acrylic Bone Cements Into Cancellous Bone", 1983.
Amstutz et al., "Warfarin Prophylaxis to Prevent Mortality From Pulmonary Embolism After Total Hip Replacement", 1989.

Primary Examiner—C. Fred Rosenbaum
Assistant Examiner—Sharon Finkel
Attorney, Agent, or Firm—Kinney & Lange

[57] ABSTRACT

The method of this invention relates to preparing a bone to secure a prosthesis thereto by improving the mechanical interdigitation of bone cement and the bone and facilitating hemostasis of the bone. First, the bone is mechanically shaped to expose cancellous bone in a desired configuration for reception of a joint prosthesis. A pressurized jet of dry-flowing gas is then applied to the exposed bone, to clean and dry the trabecular interstices of the exposed cancellous bone. To further withdraw debris and liquids dislodged from the interstices of the prepared bone by the pressurized jet of dry-flowing gas, suction is applied to the bone concurrently with the application of the pressurized jet of dry-flowing gas. Bone cement in liquid form is then applied to the bone, with cement penetration into the cleaned and dried interstices of the bone.

26 Claims, 4 Drawing Sheets

METHOD OF BONE PREPARATION FOR PROSTHETIC FIXATION

BACKGROUND OF THE INVENTION

This invention relates generally to the surgical preparation of bones for a prosthetic joint replacement, and more particularly to the use of dry flowing gas to prepare a bone bed and thereby achieve enhanced fixation of a prosthesis to the bone.

In the field of orthopedic surgery, the standard surgical technique to prepare a bone for the implantation of prosthetic components presently consists of mechanically shaping a cavity in the bone, or sculpting a surface thereon, with a variety of manual and powered tools (drills, broaches, etc.). Then, the exposed bone bed is brushed and cleaned with a saline solution for lavage and irrigation. Finally, suction is applied to remove the debris. Surgical sponges are inserted into the cavity or against the bone surface to absorb excess fluids, and thrombin-soaked foam is occasionally used in an effort to slow the bleeding. Once the bone has been so prepared, the prosthetic component is introduced therein, and may be secured to the bone by various means, including friction or force-fit into the bone cavity, bone cement and/or pins or screws.

Prosthetic joint replacements are commonly secured to the adjacent bones with a material known generically as "bone cement." Presently, the bone cement typically used is polymethyl methacrylate. The availability of such cement in the U.S. since the late 1960's has enabled joint replacement surgery to become a routine orthopedic procedure. Despite its widespread success, however, a number of problems persist with cemented joint replacements, chief among them the significant potential for long-term implant loosening, a major clinical problem which often requires another operation. Loosening may occur at either the implant-cement interface or the cement-bone interface, but the latter is both more common and more difficult to forestall. Component loosening can result from inadequate bone bed preparation; interposed fluid or surgical debris prevent the cement from penetrating into the bone to achieve good contact and stable fixation.

As mentioned above, saline lavage is used to aid in washing away the debris generated by preparation of the bone surface, and to maintain irrigation for the operative field. In traditional surgical wound debridement procedures it is taught that prolonged drying is potentially harmful to tissues. The conventional wisdom of those skilled in the art of bone preparation for prosthesis fixation has been that it is important that those portions of a patient's body exposed in a surgical procedure (including the bones) be maintained in a moist or lubricated condition to avoid damage thereto or deterioration thereof.

The use of traditional liquid flushing lavage methods for cemented joint replacement surgery, however, has been shown to be less than ideal for preparation of the cancellous portions of an exposed bone bed. The bone cleaning capacity of these methods is limited to washing debris only from the exposed bone surface. Irrigating liquid which enters the interstices of the exposed bone actually prevents any significant cleaning beneath the bone surface, due to limited access of the irrigant to the deeper interstices. Debris cannot be removed from these interstices because the liquid cannot be easily flushed in and out of these deep, interconnected spaces. Since the irrigating liquid cannot be completely removed by surgical suction, cement penetration into the bone is also impeded: the cement cannot flow into the trabecular spaces which are filled with liquid, and on the trabeculae which the cement can reach, the moisture on the bony surfaces prevents true cement-bone contact. In an attempt to address the first of these problems and to improve the efficacy of lavage in the removal of bony debris, medullary fat and hematopoietic tissue, pulsatile lavage systems such as those described in U.S. Pat. No. 4,294,251 (Greenwald et al., issued Oct. 31, 1981) and U.S. Pat. No. 4,662,829 (Nehring, issued May 5, 1987) were developed. In these systems, the traditional flushing lavage is augmented by a pulsating delivery of the irrigating fluid, resulting in improved trabecular cleaning. This may be due to the ability of the intermittent flow to temporarily interrupt the formation of hydrostatic blockages in the bony pores.

Pulsatile lavage and improved cementing techniques such as pressurized cement injection have provided improvements in prosthetic fixation, but the cement-bone interface is still problematic. Bathing the bony surface with irrigating fluids washes away the natural blood clotting factors along with the surgical debris, which hampers the effort to achieve effective control over local bleeding. Ongoing bleeding can be a major problem in achieving good contact between cement and bone. Traditional surgical methods for controlling bleeding and achieving hemostasis, such as clamping the vessel or using electrocautery, are not applicable to bone. Current practice involves time-consuming methods of limited effectiveness: most commonly, repeated applications of thrombin-soaked foam are necessary to achieve even limited hemostasis. Thrombin powder is mixed with saline at surgery; small pieces of foam are soaked in this solution and applied to the bone cavities, removing them at intervals to see if bleeding has lessened and reapplying as necessary.

Blood and irrigation fluid not removed by suction lead to an unavoidable interposed fluid phase between the cement and the bone, preventing the intimate interdigitation desired for maximum interface strength. In addition, blood mixes into the cement and impedes uniform polymerization, thereby causing laminations which weaken the cement mantle by providing possible sites of local mechanical failure. Inadequate mechanical interdigitation significantly compromises prosthesis fixation in the case of the currently available bone cement, polymethyl methacrylate, because it is essentially a grouting agent, as opposed to an adhesive. Thus, successful skeletal fixation is entirely dependent upon the intimacy, integrity and extent of the mechanical interface between the cement and the cancellous portion of the bone. Blood between the cement and bone leads to radiolucent lines visible on x-rays of the joint, which then widen in association with progressive prosthetic loosening.

An improved cement-bone interface would also be useful in procedures which involve the generic surgical use of bone cement: i.e., procedures which do not necessarily involve implant fixation. Bone cement is also used for example, in the repair or filling of bony defects in cases such as pathologic fractures, where cement may be used to secure and augment an internal fixation device. Cement has been used as a spacer, after removal of a vertebral body, or occasionally after removal of an infected prosthesis, and cement has been used in neurosurgery to fill bony defects following procedures such as craniotomy. In these various other surgical uses of bone cement, enhancement of fixation of cement to bone could also be achieved by improving the bone preparation.

As mentioned above, in some circumstances, a prosthetic component is not cemented in place, but rather engaged with the bone by friction-fit or by some mechanical fastener (e.g., screw or pin). When a prosthetic component is affixed to a bone cavity without cement, it is also important to effectively control local bleeding, from the bone, in order to minimize the various medical risks of postoperative bleeding complications. Control of local bleeding from bone, not achievable by standard techniques for hemostasis, can also be important in other procedures not involving prosthetic implantation, such as in the removal of bone tumors.

As mentioned above, conventional surgical techniques involve moistening and irrigating the tissue during surgery to prevent drying. However, it is also conventional to "dry" the surface of the prepared bone by use of an absorbent packing such as a sponge. While such packing does absorb excess fluid from the bone bed surface and may even partially dry that surface by such absorption, it does not dry or remove fluids from the interstices of cancellous bone nor does it facilitate hemostasis within the bone structure. Thus, no one has previously attempted to dry both the surface and underlying interstices of a bone bed in the course of cleaning the bone bed and preparing it for acceptance of a prosthesis component. Of course, the use of blowing gas for clearing a surface or for drying is well known, and it has been known in the field of dentistry for quite some time to use compressed air in order to improve visualization. Saliva and irrigating fluids can be removed in this manner to aid the dentist's view of a constricted area such as a tooth.

Tofflemire U.S. Pat. No. 2,812,765 and Turner U.S. Pat. No. 3,208,145 illustrate devices which each combine into a single instrument three separate lines for providing irrigation, suction, and compressed gas: standard dental procedures which previously had required the use of three separate instruments. The Tofflemire patent also refers to the use of carbon dioxide gas as opposed to air. Carbon dioxide is widely used in other medical applications such as arthroscopy or gynecological laparoscopy (see, e.g., U.S. Pat. No. 4,735,603), and the safety of carbon dioxide use in the body is well documented.

SUMMARY OF THE INVENTION

Classical surgical procedure in orthopedics and other surgical disciplines has always emphasized the importance of heavy and continuous irrigation of body tissues. Contrary to this conventional wisdom, the present invention is based on the finding that dry flowing gas directed at and into the sculpted bony bed is efficacious for site-specific preparation of the bone immediately prior to prosthetic implantation. When a bone cement is also used, the use of gas in bone preparation leads to increased mechanical interdigitation of cement with bone, by (a) better debris removal, (b) removal of liquids from the "wells" between the trabeculae, (c) drying the trabeculae, and (d) facilitating hemostasis which saves surgical time as well. These factors then lead to enhanced long-term prosthetic fixation.

In one preferred embodiment, the inventive method improves mechanical interdigitation of bone cement and a bone by first mechanically shaping a bone surface, which includes exposed cancellous bone, for reception of a joint prothesis. Then, a pressurized jet of dry flowing gas is applied to the bone surface, to clean and dry the trabecular interstices of the exposed cancellous bone. Bone cement is then forced into the dried interstices of the bone.

In another preferred embodiment, the inventive method improves cement penetration and bond strength of a prosthetic fixation, such as an implant, with a bone. First, a bone surface which includes exposed cancellous bone is mechanically shaped for reception of the implant. Then a pressurized jet of dry flowing gas is applied to the prepared bone to clean and dry the bone, and the implant is then cemented into the prepared bone, with cement penetration into the cleaned and dried interstices of the bone.

In a still further embodiment, the inventive method facilitates hemostasis of a surgically prepared bone. To do so, trabecular interstices of the prepared bone are exposed to a pressurized jet of dry flowing gas to substantially remove debris and liquids from the prepared bone, providing a dry environment and thereby enabling natural rapid coagulation.

DETAILED DESCRIPTION OF THE PREFERRED EMBODIMENTS

In any implant prosthesis fixation, the bone or bones to which the implant will be affixed must be prepared. Said preparation may involve simply sculpting the bone to a desired shape, or the creation of a relatively deep cavity in the bone for reception of a portion of the implant therein. This sculpting and cavity creation are done mechanically, and sometimes includes sawing away portions of the bone away for access. The cavity may be reamed or brushed out using manual or powered drills or reamers until a desired shape is achieved for reception of a component of a prosthesis joint.

Figures 1, 2:
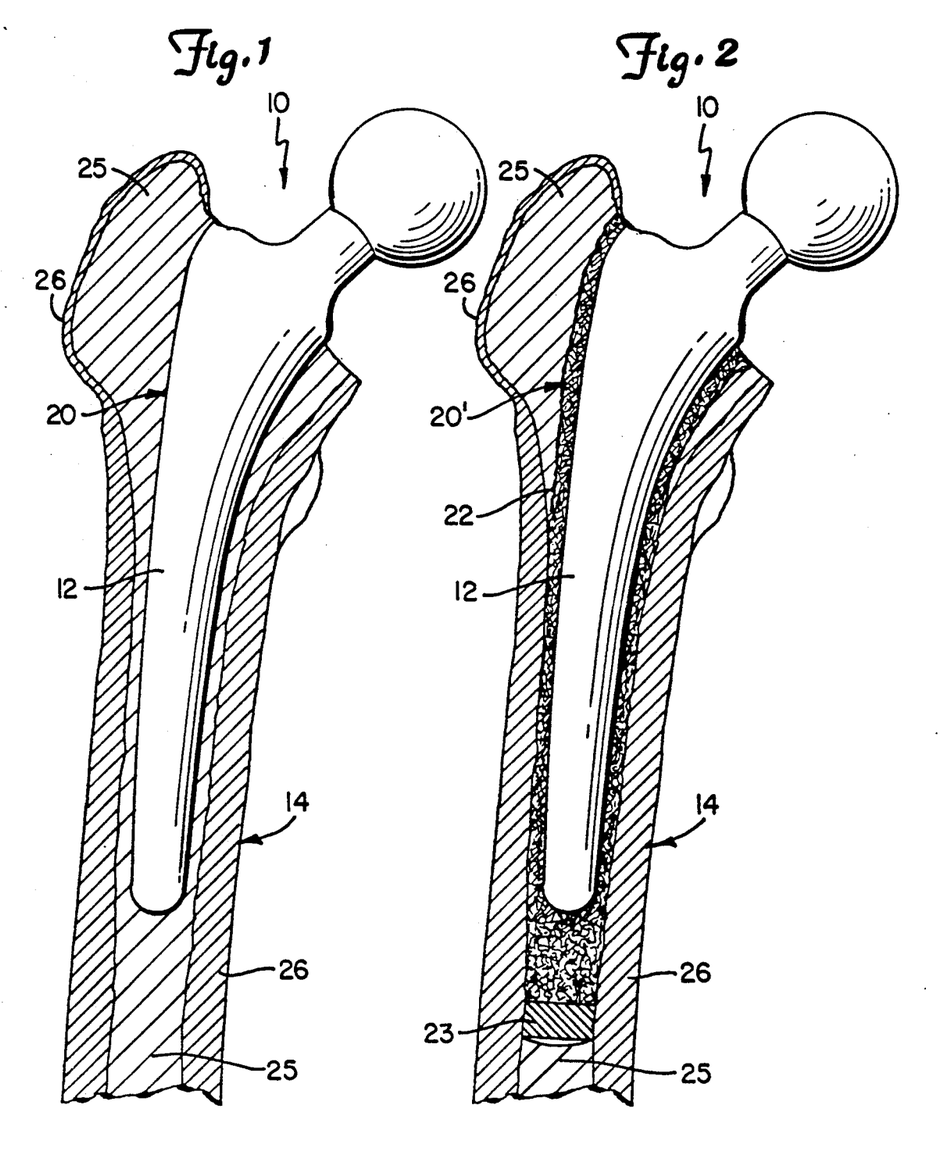
FIG. 1 is a cross-sectional illustration of a a prosthesis stem component friction-fit therein.
FIG. 2 is a sectional view of a femur having a prosthesis stem component cemented into a bone cavity therein.

FIGS. 1 and 2 illustrate the typical types of cavities and bone sculpturing which may be necessary. While these FIGS. illustrate a femur, it is understood that the method of bone preparation of the present invention is suitable for application to other bones as well.

FIGS. 1 and 2 illustrate a joint prosthesis 10 having its femoral stem component 12 inserted into the medullary canal of a femur 14. In FIG. 1, a cavity 20 has been shaped in the femur 14 for a close friction-fit of the stem component 12. In FIG. 2, a cavity 20' is formed, larger than the stem component 12, for the additional acceptance of bone cement 22 (e.g., polymethyl methacrylate) therein.

In either case, the shaping of the bone for reception of the prosthetic joint component exposes cancellous portions of the bone at the surface of the bone bed or cavity. These cancellous portions of the bone are sponge-like in structure, having numerous interconnected interstices. In FIGS. 1 and 2, these cancellous portions of the femur are illustrated generally as the broader cross-sectional areas, indicated as at 25, while the cortical or solid portions of the femur (its outermost portions) are illustrated generally as the denser cross-sectional areas, indicated at 26. To a great extent, therefore, it is the exposed cancellous portions of the bone that the prosthetic component is in direct contact with or must be affixed to for a complete and proper fixation. As seen in FIG. 2, a cement restrictor 23 (a plug of bone or plastic) is used to allow for pressurizing the cement 22 in the femur 14 without driving the cement 22 through the bone all the way down to the knee. The restrictor 23 is typically placed into the cavity 20', about 2 cm beyond the distal tip of the stem component 12.

As may be readily appreciated, the mechanical shaping of a bone for acceptance of a prosthetic joint component can create a large amount of debris in the surgical field. Such debris will include blood, other body fluids and soft tissue and of course, bone debris, medullary fat and hematopoietic tissue. Typically, these materials have been cleared from the surgical field by washing the area and then suctioning away the wash fluid and debris. This procedure, referred to as surgical lavage, does remove a significant portion of the unwanted materials, but is not a complete cleaning in any regard. One attempt to improve the suction lavage procedure is by providing a pulsed jet of lavage solution, which is directed at the exposed cancellous portions of the bone to "blast" any debris and unwanted materials therefrom, while simultaneously providing suction to remove those materials from the surface of the bone bed.

While the ends of cleaning and irrigation are achieved by the use of suction lavage during prosthetic surgery, the fact that some debris remains, along with the fact that the lavage solution itself remains also creates problems. Any remaining debris and lavage solution in the spaces between the bony trabeculae interfere with cement penetration, thereby preventing the complete interdigitation of bone cement into the cancellous portions of the bone. Consequently, the connection between the bone cement and the bone may be weaker than possible, and as a result, the connection between the bone and the prosthetic component being affixed thereto is not as strong and durable as desired. The connection desired between bone and bone cement is a complex interdigitation of the two materials, resulting in a strong transition zone consisting of a bone/bone cement composite material.

As mentioned above, sponges have been employed to "dry" the bone surface prior to cement application. Such absorbent materials do not remove fluids from the trabecular interstices of the bone, however, and at best simply soak up fluids disposed on the exposed bone surface. Such absorbent materials thus fail to effectively dry the bone for acceptance of bone cement, nor are they effective in facilitating hemostasis.

To counteract these problems, the present invention provides certain additional steps to the preparation of a bone for a prosthetic implantation. Once the bone bed has been sculpted to its desired shape, a pressurized jet of sterile dry flowing gas is applied to the bone surface. This jet of pressurized gas cleans and dries the surface of the bone and also the trabecular interstices of the exposed cancellous portions of the bone by forcing any remaining debris, liquids or other unwanted tissue therefrom. This blast of gas simply "blows out" the debris from the interstices of the bone and at the same time, blows out any liquids therein to dry the bone bed. The gas flow can be a steady stream or an oscillating or pulsatile flow as desired.

Preferably, the gas is carbon dioxide, which has been demonstrated to be safe for use within the body. The very high diffusion coefficient of carbon dioxide causes it to present a significantly lower risk of embolism as compared to the use of nitrogen or oxygen, for example. Medical grade carbon dioxide is available in most operating room settings, either from a wall-mounted fixture or from a separate pressurized tank of carbon dioxide. While carbon dioxide is the preferred gas, the advantages achieved by use of the present inventive method could also be attained by the use of other dry gases.

The advantages of using a dry flowing gas in bone preparation are many. A focused flow of gas is helpful for removing small particles of debris from within the cancellous structure of the bone. Gas is less messy than a liquid, and is more effective in removing blood and other liquids than an irrigant or lavage solution. The gas, which flows over the bone bed surface and throughout the trabecular interstices of the bone, also dries the bone while cleaning it, thereby eliminating the possibility of an interposed fluid or liquid phase between the bone and a prosthesis component and/or the bone cement. While drying the bone is contrary to the traditional view that exposed tissue should always remain moist, it is believed that the advantages in coagulation, cleaning and resultant bone-bone cement interface are such that a slight dry period for the bone is acceptable during surgery. Use of the present method for achieving hemostasis can present a significant advantage in decreased surgical time, as compared with current hemostasis methods (i.e., the application of thrombin-soaked foam).

An additional advantage from using a dry flowing gas in bone preparation is that the bone cement may be applied in liquid form and achieve a higher penetration into the bone than would otherwise be possible. The type of bone cement typically used in prosthetic fixation surgery is, as mentioned above, polymethyl methacrylate, and it is typically introduced to the bone in a doughlike form during hardening. In use, the cement is provided in two components: a powder component which is then mixed with a liquid component prior to application. After mixing, the initial consistency of the cement is like that of a batter. As the cement polymerizes, it hardens first to a dough-like consistency, and eventually to a hardened material which is actually so hard it cannot be effectively manipulated and forced into the bone. By cleaning and drying the bone with a dry flowing gas, the bone cement can be applied in liquid (batter) form and thus can achieve a greater penetration into the dried trabeculae of the bone. Indeed, capillary action of the liquid cement actually "pulls" the cement along into the bone. Accordingly, greater cement penetration into the cancellous portion of the bone results in a stronger bond between the prosthesis and bone.

The jet of pressurized dry flowing gas is delivered by a suitable nozzle connected to the gas source. Such a nozzle is manipulatable to direct the jet of pressurized gas into a relatively narrow cavity to a desired location for a local cleaning and drying. The application of the pressurized gas through the nozzle and to the bone is thereby controlled by the surgeon to achieve the cleaning and drying effect desired. With respect to the present inventive method, the actual configuration and operation of the delivery nozzle for the jet of pressurized gas is not critical, only that the jet be deliverable as specified to the surface of the bone bed.

Figure 3:
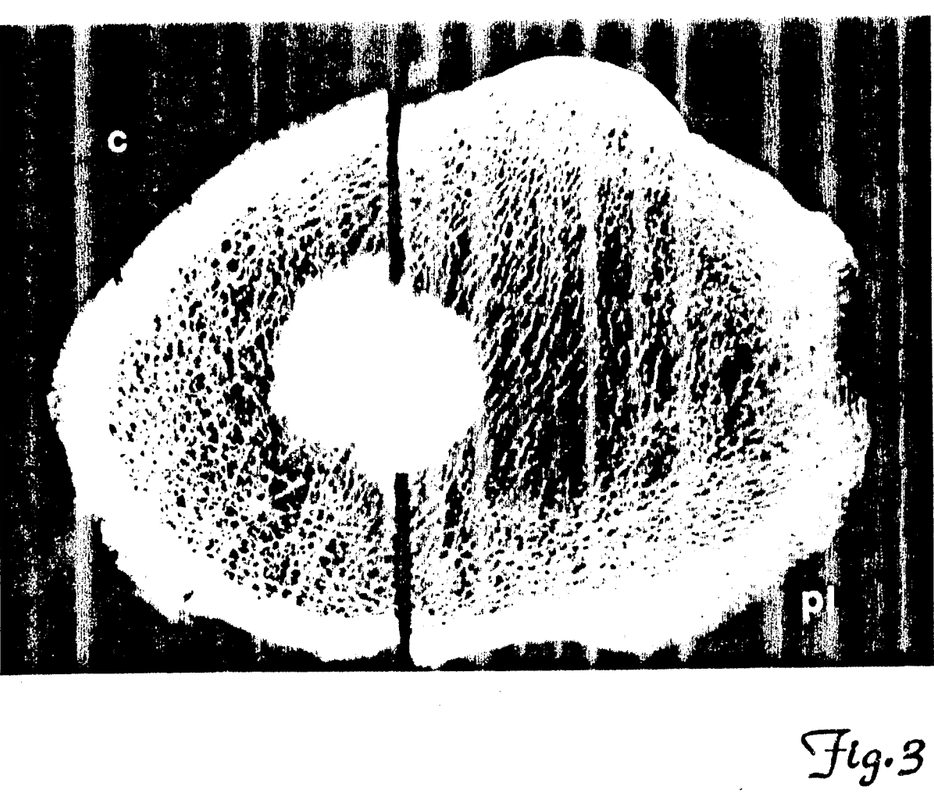
FIG. 3 is a black-and-white enlarged photograph of a cross-section through a tibia showing the cancellous structure of the bone and showing a comparison of bone cement penetration when the present invention is employed, and when pulsed lavage is employed.
Figure 4:
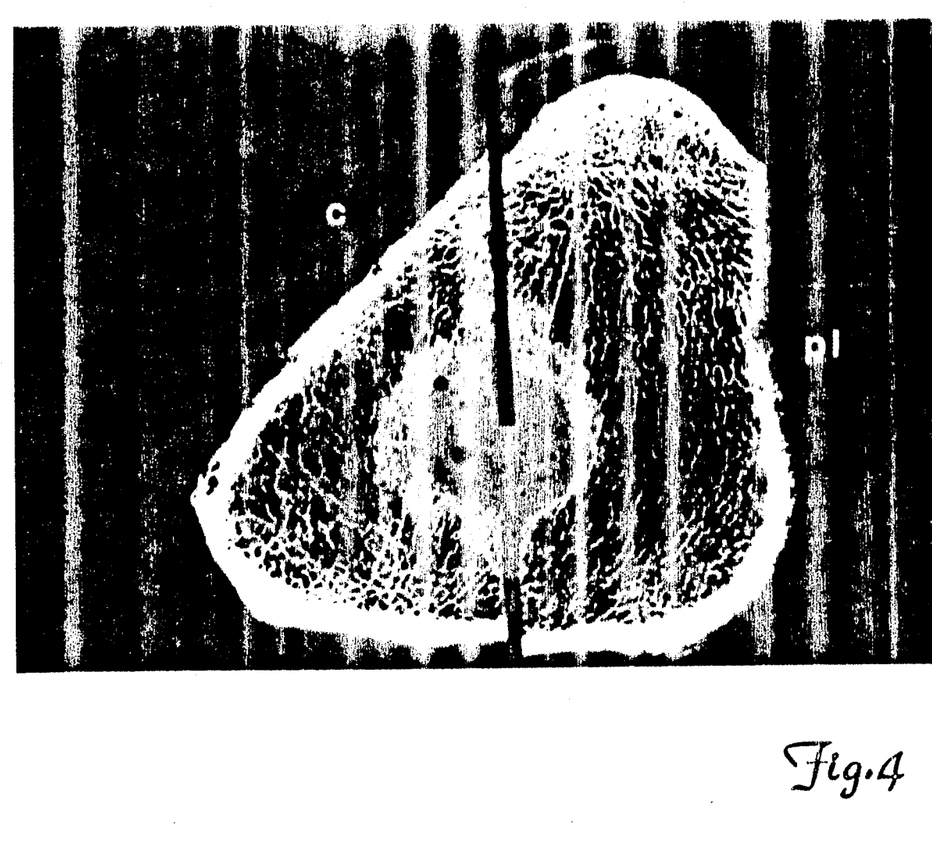
FIG. 4 is another black-and-white enlarged photograph of a cross-section through a tibia showing the cancellous structure of the bone and showing a comparison of bone cement penetration when the present invention is employed, and when pulsed lavage is employed.
Figure 5:
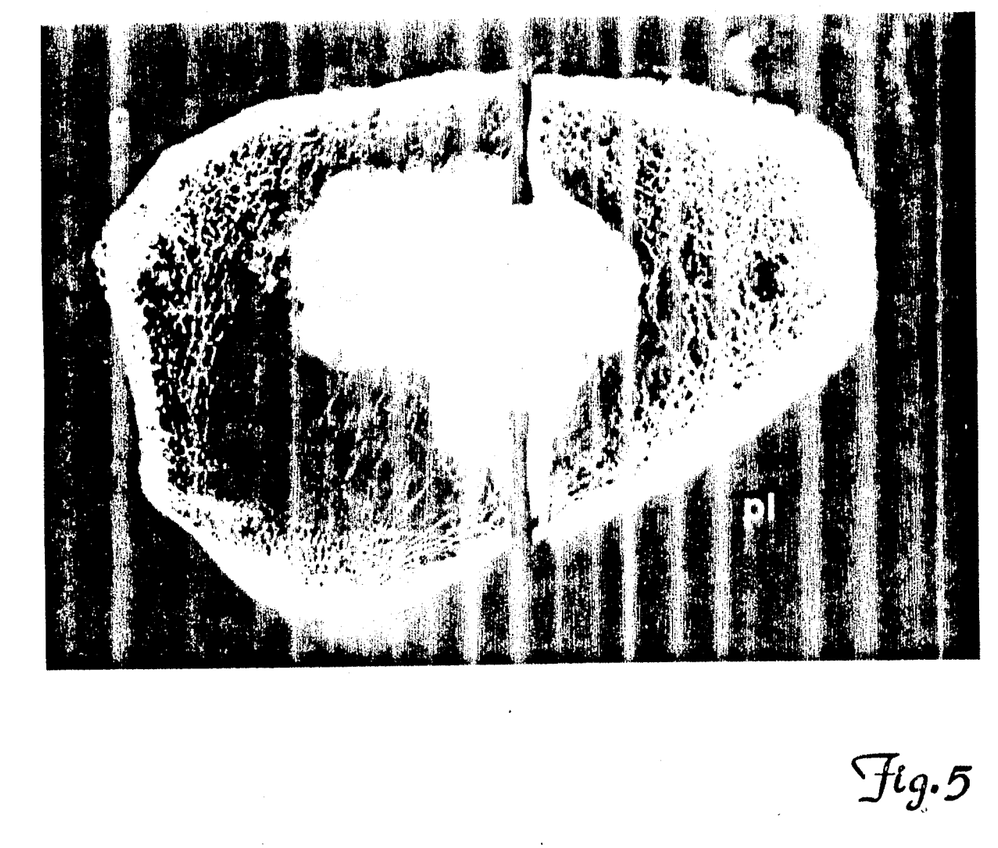
FIG. 5 is another black-and-white enlarged photograph of a cross-section through a tibia showing the cancellous structure of the bone and showing a comparison of bone cement penetration when the present invention is employed, and when pulsed lavage is employed.

FIGS. 3, 4 and 5 illustrate, by photographs, a representative comparison of bone cement penetration between a bone prepared using suction lavage only, and a bone bed prepared with a jet of pressurized dry flowing gas. Each photograph illustrates a cross-section of a portion of a tibia which was centrally reamed and then sawed longitudinally in half. In each FIG., the right "half" of the bone had the reamed bone bed prepared for cement application by a pulsed lavage technique, while the left "half" of each bone section had its reamed bone bed prepared for cement application by exposure to a pressurized jet of dry flowing gas. After preparing the bone bed sections in this manner, the bone halves were secured together, and bone cement was forced into the reamed cavity in the same manner as if preparing for acceptance of a joint prosthesis.

After the bone cement hardened, the bone was sawed into transverse sections, as illustrated in FIGS. 3, 4 and 5. As is readily apparent in a comparison of the differently treated halves of the tibia, cement penetration into the cancellous portions of the bone is much greater when the bone bed is prepared using a pressurized jet of dry flowing gas than when a pulsed lavage preparation is used. Radiographic and visual inspection of the specimens demonstrated at least a forty percent greater penetration of cement into the trabecular interstices of the bone, as fully illustrated in FIGS. 3, 4 and 5. Accordingly, deeper penetration of the cement into the bone bed leads to a greater fixation of the bone cement to the bone and consequently, a better fixation of the prosthesis component to the bone as well.

Concurrently with the application of the pressurized jet of dry flowing gas, suction can be applied to facilitate the removal of debris and liquids dislodged from the interstices of the prepared bone by the gas.

The inventive method can be employed, at a surgeon's discretion, either as a final step in the standard cleaning/irrigation procedure, or used as the sole cleaning method following the mechanical shaping and brushing of the bone cavity. Laboratory testing, as illustrated in FIGS. 3, 4 and 5 and in the example below, has demonstrated that the flowing gas can remove debris which is unaffected by pulsatile lavage, effectively cleaning deeper recesses of the interconnected cancellous bone network and therefore permitting enhanced bone cement penetration and interdigitation.

As mentioned above, the application of a pressurized jet of dry flowing gas presents yet another advantage in its use, that of enhancing coagulation in the surgical field. The application of the pressurized gas creates local drying (both on the exposed bone bed surface and within the trabecular interstices of the bone), which evaporates any remaining irrigation fluid and allows the natural blood clotting process to occur in the venous sinusoids of the bone. This in turn should minimize the possibility of blood or other fluids mixing into the cement and thereby weakening the cement mantle by providing sites of local mechanical failure where the cement has not become uniformly polymerized. Effective hemostasis can also help to minimize postoperative complications associated with localized bleeding.

EXAMPLE

In order to determine the extent of increased cement penetration achieved by the use of the present invention for preparing the cancellous bone bed to receive a cemented prosthesis, a controlled study was conducted in the laboratory comparing the application of a pressurized jet of dry flowing gas to pulsed lavage cleaning, the state of the art in surgical cleaning techniques.

Adult human cadaveric tibiae were selected for the study. A $\frac{1}{2}$ diameter hole was drilled axially into the intramedullary canal. The bones were sectioned longitudinally through this hole and the two halves were laid open for cleaning. One side was subjected to 15 seconds of pulsed lavage cleaning; the other was cleaned for 15 seconds with a pressurized jet of carbon dioxide, using a gas flow rate of approximately 2.5 CFM. The two bone halves were then reassembled, and polymethyl methacrylate (PMMA) bone cement was injected and pressurized into the reassembled intramedullary canal, using standard surgical cementing techniques. Thus all parameters of bone preparation and cement delivery were identical for these specimens with the exception of the cleaning method chosen.

The most evident difference in the test samples was the volume of cement which penetrated across the prepared surfaces. FIGS. 3, 4 and 5 illustrate samples from this study. Those portions of the bone specimens cleaned and dried with the gas show substantially greater cement penetration than those prepared merely with pulsed lavage.

SUMMARY

The present invention provides an improved method for preparation of a cancellous bone bed for implantation of a joint replacement prosthesis, or other surgical constructs involving the use of bone cement. The method of the invention leads to safe and effective cleaning of the medullary cavity and the trabecular interstices and removal of excess fluids and tissue, while also aiding the surgeon in achieving hemostasis rapidly, by permitting the natural blood clotting agents to act. These advantages are accomplished by applying a pressurized jet of dry flowing gas to the exposed cancellous portions of a prepared bone surface to clean and dry the trabecular interstices thereof.

Although the present invention has been described with reference to preferred embodiments, workers skilled in the art will recognize that changes may be made in form and detail without departing from the spirit and scope of the invention.

What is claimed is:

1. A method to improve mechanical interdigitation of bone cement and a prepared bone which comprises the steps of:
   mechanically shaping a bone surface, which includes exposed cancellous bone, for reception of a joint prosthesis;

applying a pressurized jet of dry flowing gas having a relatively high diffusion coefficient relative to oxygen or nitrogen to the bone surface, to clean and dry the trabecular interstices of the exposed cancellous bone; and forcing bone cement into the dried interstices of the bone.

2. The method of claim 1, and further comprising the step of:

washing the bone with a lavage solution prior to application of the pressurized jet of dry flowing gas.

3. The method of claim 2, and further comprising the step of:

applying suction to the bone to withdraw surface debris and the lavage solution prior to application of the pressurized jet of dry flowing gas.

4. The method of claim 1, and further comprising the step of:

applying suction to the bone to initially withdraw liquids and debris therefrom prior to application of the pressurized jet of dry flowing gas.

5. The method of claim 1, and further comprising the step of:

applying suction to the bone concurrently with the application of the pressurized jet of dry flowing gas to withdraw debris and liquids dislodged from the interstices of the prepared bone by the application of the pressurized jet of dry flowing gas.

6. The method of claim 1, wherein the dry flowing gas is carbon dioxide.

7. The method of claim 1 wherein the bone cement, at the time of application thereof to the bone, is in a liquid state.

8. The method of claim 1, and further comprising the step of:

pulsating the pressurized jet of dry flowing gas.

9. A method to improve cement penetration and bond strength of a prosthetic fixation, such as an implant, with prepared bone, comprising the steps of:

mechanically shaping a bone surface, which includes exposed cancellous bone, for reception of the implant;

applying a pressurized jet of dry flowing gas having a relatively high diffusion coefficient relative to oxygen or nitrogen to the prepared bone surface to clean and dry the bone; and pressure cementing the implant into the prepared bond, with cement penetration into the cleaned and dried interstices of the bone.

10. The method of claim 9, and further comprising the step of:

washing the bone with a lavage solution prior to application of the pressurized jet of dry flowing gas.

11. The method of claim 10, and further comprising the step of:

applying suction to the bone to withdraw surface debris and the lavage solution prior to application of the pressurized jet of dry flowing gas.

12. The method of claim 9, and further comprising the step of:

applying suction to the bone to initially withdraw liquids and debris therefrom prior to application of the pressurized jet of dry flowing gas.

13. The method of claim 9, and further comprising the step of:

applying suction to the bone concurrently with the application of the pressurized jet of dry flowing gas to withdraw debris and liquids dislodged from the interstices of the prepared bone by the application of the pressurized jet of dry flowing gas.

14. The method of claim 9, wherein the dry flowing gas is carbon dioxide.

15. The method of claim 9 wherein during the pressure cementing step, the cement is initially introduced to the bone in a liquid state.

16. The method of claim 9, and further comprising the step of:

pulsating the pressurized jet of dry flowing gas.

17. A method of facilitating hemostasis of surgically prepared bone, comprising the step of:

exposing the trabecular interstices of the prepared bone to a pressurized jet of dry flowing gas having a relatively high diffusion coefficient relative to oxygen or nitrogen, to substantially remove debris and liquids from the prepared bone, thereby enabling natural rapid coagulation.

18. The method of claim 17, and further comprising the step of:

washing the bone with a lavage solution prior to the exposure thereof to the pressurized jet of dry flowing gas.

19. The method of claim 18, and further comprising the step of:

applying suction to the bone to withdraw surface debris and the lavage solution prior to the exposure of the bone to the pressurized jet of dry flowing gas.

20. The method of claim 17, and further comprising the step of:

applying suction to the bone to initially withdraw liquids and debris therefrom prior to the exposure of the bone to the pressurized jet of dry flowing gas.

21. The method of claim 17, and further comprising the step of:

applying suction to the bone concurrently with the exposure of the bone to the pressurized jet of dry flowing gas, to withdraw debris and liquids dislodged from the interstices of the prepared bone by pressurized jet of dry flowing gas.

22. The method of claim 17, wherein the dry flowing gas is carbon dioxide.

23. The method of claim 17, and further comprising the step of:

oscillating the flow of the pressurized jet of dry flowing gas.

24. In a process for preparing a bone for the application of bone cement thereto, where a surface of the bone has been shaped to expose cancellous bone with trabecular interstices therein, the improvement which comprises:

applying a pressurized jet of dry flowing carbon dioxide to the shaped bone surface to clean and dry the trabecular interstices of the exposed cancellous bone so that the mechanical interdigitation of the bone cement and the bone is improved when the bone cement is later forced against the bone surface and into the trabecular interstices thereunder.

25. The process of claim 24 wherein the bone cement, at the time of application thereof to the bone, is in a liquid state.

26. In a process for preparing a bone for the application of bone cement thereto, where a surface of the bone has been shaped to expose cancellous bone with trabecular interstices therein, the improvement which comprises:

applying a pressurized jet of dry flowing gas having a relatively high diffusion coefficient relative to oxygen or nitrogen to the shaped bone surface to clean and dry the trabecular interstices of the exposed cancellous bone so that the mechanical interdigitation of the bone cement and the bone is improved when the bone cement is later forced against the bone surface and into the trabecular interstices thereunder.

* * * * *

REEXAMINATION CERTIFICATE (3488th)
United States Patent [19]

Matsen, III

[11] B1 5,037,437

[45] Certificate Issued Apr. 14, 1998

[54] METHOD OF BONE PREPARATION FOR PROSTHETIC FIXATION

[75] Inventor: Frederick A. Matsen, III, Seattle, Wash.

[73] Assignee: The University of Washington, Seattle, Wash.

Reexamination Request:
No. 90/004,032, Nov. 14, 1995

Reexamination Certificate for:
Patent No.: 5,037,437
Issued: Aug. 6, 1991
Appl. No.: 466,777
Filed: Jan. 18, 1990

[51] Int. Cl.$^6$ .................................................. A61F 2/028
[52] U.S. Cl. .................................................. 623/16
[58] Field of Search .............................. 604/35, 49, 54, 604/93, 119, 902; 128/897, 898; 433/180, 183; 623/16, 18, 19, 20, 22, 23; 606/53, 86

[56] References Cited

U.S. PATENT DOCUMENTS 4,215,984   8/1980   Reichley.
4,619,612  10/1986   Weber et al..

OTHER PUBLICATIONS

Noble et al. Penetration of Acrylic Bone Cements Into Cancellous Bone, *Acta Orthop. Scand.* vol. 54, pp. 566–573 (1983).

Cooke et al., "The Influence of Surgical Technique on the Strength of Cement Fixation", *Orthopaedic Transactions*, published by *The Journal of Bone and Joint Surgery*, vol. 2, No. 1, pp. 128–129 (1978).

Schurman et al., "Embolization From Bone", *27th Annual ORS, Las Vegas, Nevada*, p. 205 (1981).

Harvey et al., "Prevention of Air Emboli in Hip Surgery—Femoral Shaft Insufflation With Carbon Dioxide", *Anesthesia*, vol. 37, pp. 714–717 (1982).

*Primary Examiner*—Guy V. Tucker

[57] ABSTRACT

The method of this invention relates to preparing a bone to secure a prosthesis thereto by improving the mechanical interdigitation of bone cement and the bone and facilitating hemostasis of the bone. First, the bone is mechanically shaped to expose cancellous bone in a desired configuration for reception of a joint prosthesis. A pressurized jet of dry-flowing gas is then applied to the exposed bone, to clean and dry the trabecular interstices of the exposed cancellous bone. To further withdraw debris and liquids dislodged from the interstices of the prepared bone by the pressurized jet of dry-flowing gas, suction is applied to the bone concurrently with the application of the the pressurized jet of dry-flowing gas. Bone cement in liquid form is then applied to the bone, with cement penetration into the cleaned and dried interstices of the bone.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 17–23 are cancelled.

Claims 1, 9, 24 and 26 are determined to be patentable as amended.

Claims 2–8, 10–16 and 25, dependent on an amended claim, are determined to be patentable.

1. A method to improve mechanical interdigitation of bone cement and a prepared bone which comprises the steps of:
   mechanically shaping a bone surface, which includes exposed cancellous bone, for reception of a joint prosthesis;
   applying a pressurized jet of dry flowing gas having a relatively high diffusion coefficient relative to oxygen or nitrogen to the bone surface, *at a flow rate sufficient* to clean *debris from the trabecular interstices of the exposed cancellous bone* and dry the trabecular interstices of the exposed cancellous bone; and
   forcing bone cement into the dried interstices of the bone.

9. A method to improve cement penetration and bond strength of a prosthetic fixation, such as an implant, with prepared bone, comprising the steps of:
   mechanically shaping a bone surface, which includes exposed cancellous bone, for reception of the implant;
   applying a pressurized jet of dry flowing gas having a relatively high diffusion coefficient relative to oxygen or nitrogen to the prepared bone surface *at a flow rate sufficient* to clean *debris from the exposed cancellous bone* and dry the bone; and
   pressure cementing the implant into the prepared bone, with cement penetration into the cleaned and dried interstices of the bone.

24. In a process for preparing a bone for the application of bone cement thereto, where a surface of the bone has been shaped to expose cancellous bone with trabecular interstices therein, the improvement which comprises:
   applying a pressurized jet of dry flowing carbon dioxide to the shaped bone surface *at a flow rate sufficient* to clean *debris from the trabecular interstices of the exposed cancellous bone* and dry the trabecular interstices of the exposed cancellous bone so that the mechanical interdigitation of the bone cement and the bone is improved when the bone cement is later forced against the bone surface and into the trabecular interstices thereunder.

26. In a process for preparing a bone for the application of bone cement thereto, where a surface of the bone has been shaped to expose cancellous bone with trabecular interstices therein, the improvement which comprises:
   applying a pressurized jet of dry flowing gas having a relatively high diffusion coefficient relative to oxygen or nitrogen to the shaped bone surface *at a flow rate sufficient* to clean *debris from the trabecular interstices of the exposed cancellous bone* and dry the trabecular interstices of the exposed cancellous bone so that the mechanical interdigitation of the bond cement and the bone is improved when the bone cement is later forced against the bone surface and into the trabecular interstices thereunder.

* * * * *